(12) United States Patent
Blacklock

(10) Patent No.: US 12,076,477 B2
(45) Date of Patent: Sep. 3, 2024

(54) SURGICAL SUCTION DEVICE

(71) Applicant: Christopher Stephen Blacklock, Sidlesham (GB)

(72) Inventor: Christopher Stephen Blacklock, Sidlesham (GB)

(*) Notice: Subject to any disclaimer, the term of this patent is extended or adjusted under 35 U.S.C. 154(b) by 0 days.

(21) Appl. No.: 17/857,524

(22) Filed: Jul. 5, 2022

(65) Prior Publication Data

US 2023/0009147 A1   Jan. 12, 2023

(30) Foreign Application Priority Data

Jul. 6, 2021 (IT) .......................... 102021000017777

(51) Int. Cl.
*A61M 1/00* (2006.01)
(52) U.S. Cl.
CPC ..................................... *A61M 1/87* (2021.05)
(58) Field of Classification Search
CPC ............. A61M 1/84; A61M 1/86; A61M 1/87
See application file for complete search history.

(56) References Cited

U.S. PATENT DOCUMENTS

| | | | | |
|---|---|---|---|---|
| 3,528,427 A * | 9/1970 | Sheridan | ............... | A61M 27/00 604/45 |
| 3,771,527 A * | 11/1973 | Ruisi | ...................... | A61M 1/85 604/96.01 |
| 4,068,664 A * | 1/1978 | Sharp | ...................... | A61M 1/84 433/91 |
| 4,767,404 A * | 8/1988 | Renton | .................... | A61M 1/84 604/48 |
| 5,171,223 A | 12/1992 | Herzberg | | |
| 5,236,414 A * | 8/1993 | Takasu | ............. | A61B 17/22012 601/3 |
| 5,605,537 A * | 2/1997 | Ivey | ................... | A61B 17/3203 604/27 |
| 2002/0010416 A1* | 1/2002 | Uflacker | ................ | A61M 1/85 604/35 |

(Continued)

OTHER PUBLICATIONS

PVC Profile | Intek Plastics. (Jun. 9, 2022). Intek Plastics, LLC. https://www.intekplastics.com/materials-guide/flexible-pvc/ (Year: 2020).*

(Continued)

*Primary Examiner* — Rebecca E Eisenberg
*Assistant Examiner* — Hans Kaliher
(74) *Attorney, Agent, or Firm* — NIXON & VANDERHYE

(57) ABSTRACT

A surgical suction device (10) comprising:
a connector (12),
a surgical cavity insertion tube (14), and
a suction tip (16),
wherein the surgical cavity insertion tube (14) is connected at a proximal end thereof to the connector (12) and at a distal end thereof to the suction tip (16), and the suction tip (16) comprises an inner hollow shaft (18) and an outer hollow shaft (20) coaxial to each other, the inner hollow shaft (18) having a first central opening (22) at a distal end thereof, and the outer hollow shaft (20) having an end wall (24) at a distal end thereof, wherein the end wall (24) has a second central opening (26) in axial alignment with the first central opening (22) of the inner hollow shaft (18), wherein the outer hollow shaft (20) has one or more openings (28) on a lateral wall (30) thereof.

13 Claims, 3 Drawing Sheets

(56) References Cited

U.S. PATENT DOCUMENTS

| | | | |
|---|---|---|---|
| 2006/0100605 A1* | 5/2006 | Bicakci | A61M 1/84 604/264 |
| 2010/0152707 A1* | 6/2010 | Morris | A61M 1/84 604/523 |
| 2018/0056048 A1* | 3/2018 | Guedes de Campos | A61M 25/0028 |

OTHER PUBLICATIONS

Search Report and Written Opinion for Italian Patent Application No. 102021000017777, dated Mar. 25, 2022 (7 pages).

* cited by examiner

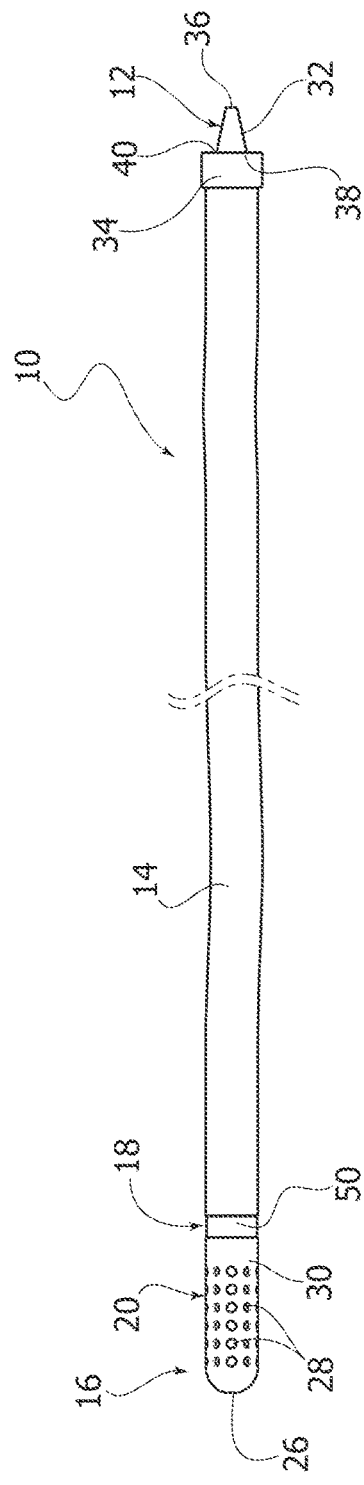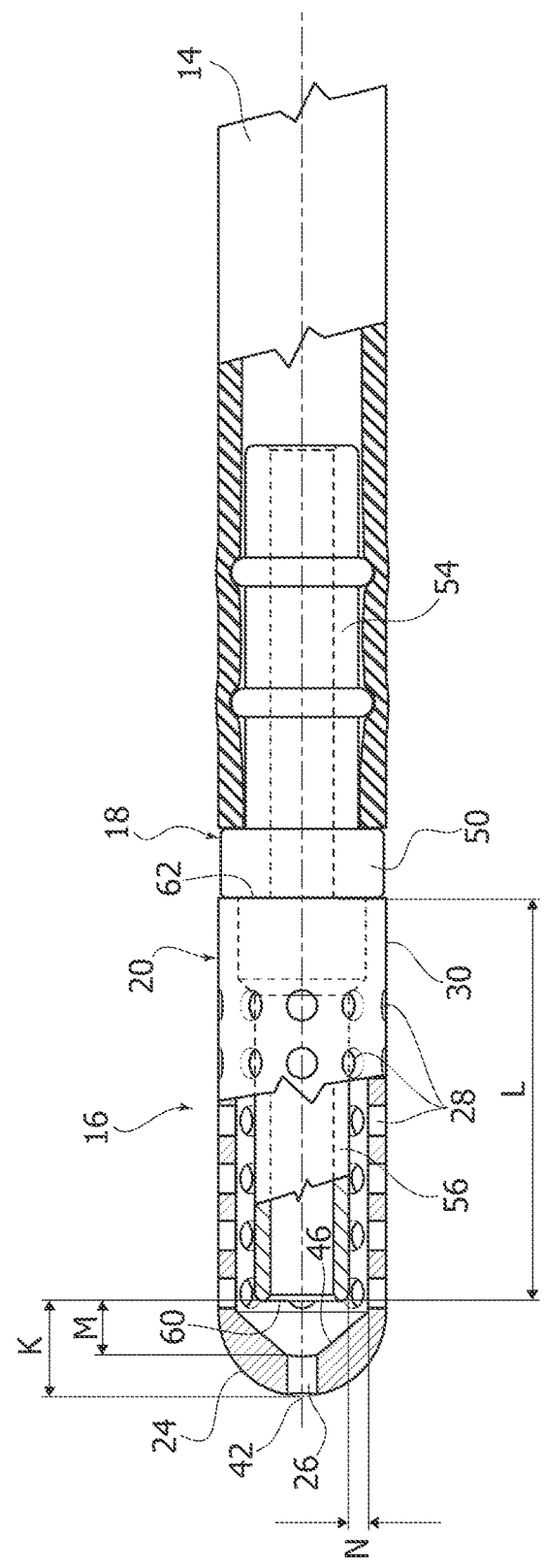

SURGICAL SUCTION DEVICE

This application claims priority to IT 102021000017777 filed Jul. 6, 2021, the entire contents of which is hereby incorporated by reference.

FIELD OF THE INVENTION

The present description concerns a surgical suction device.

BACKGROUND ART

The suction of blood, cleaning liquid, and body fluid during a surgical operation is a very important manoeuvre for ensuring a surgical view and is involved in the safety and precision of the surgical operation.

Many surgical suction devices have been designed over the years, nevertheless many of them showed failings. These are often in the design of the devices as they are either not efficient enough, that is, they leave too much fluid in the surgical field, or can potentially suck on tissue and cause trauma, or also draw in a lot of air which mixes with the blood and therefore creates the risk of micro emboli and haemolysis.

There is therefore the need of improved surgical suction devices which reduce as much as possible the above identified failings.

SUMMARY OF THE INVENTION

The object of this disclosure is to provide a surgical suction device which overcomes the drawbacks of the known devices.

According to the invention, the above object is achieved thanks to the subject matter recalled specifically in the ensuing claims, which are understood as forming an integral part of this disclosure.

In one embodiment, the present invention concerns a surgical suction device 10 comprising:
- a connector 12,
- a surgical cavity insertion tube 14, and
- a suction tip 16, wherein the surgical cavity insertion tube 14 is connected at a proximal end thereof to the connector 12 and at a distal end thereof to the suction tip 16, wherein the suction tip 16 comprises an inner hollow shaft 18 and an outer hollow shaft 20 coaxial to each other, the inner hollow shaft 18 having a first central opening 22 at a distal end thereof, and the outer hollow shaft 20 having an end wall 24 at a distal end thereof, wherein the end wall 24 has a second central opening 26 in axial alignment with the first central opening 22 of the inner hollow shaft 18, and wherein the outer hollow shaft 20 has one or more openings 28 on a lateral wall 30 thereof.

The design of the surgical suction device 10 object of the present disclosure has taken into account the risk factors involved in using surgical suction and minimised them as well as ensuring that the device functions as efficiently as possible with little interaction from the surgical team using the device.

BRIEF DESCRIPTION OF THE DRAWINGS

The invention will now be described in detail, purely by way of an illustrative and non-limiting example and, with reference to the accompanying drawings, wherein:

FIG. 1 is a plan view of the surgical suction device according to the present invention;

FIG. 2 is a sectional view of a distal end portion of the surgical suction device according to the present invention;

DETAILED DESCRIPTION OF THE INVENTION

Figure 4:
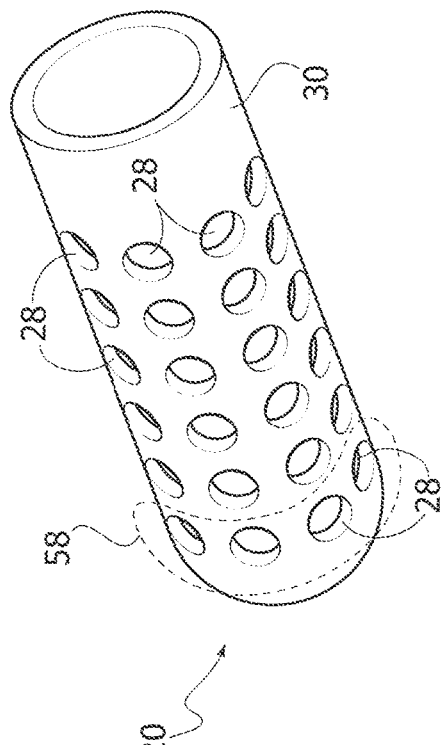
FIG. 4 is a perspective view of the outer hollow shaft of FIG. 3.

In the description that follows, numerous specific details are given to provide a thorough understanding of the embodiments. The embodiments can be practiced without one or more of the specific details, or with other methods, components, materials, etc. In other instances, well-known structures, materials, or operations are not shown or described in detail to avoid obscuring aspects of the embodiments.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The headings provided herein are for convenience only and do not interpret the scope or meaning of the embodiments.

In the present description some dimensional parameters are provided. It is intended that dimensional tolerances are to be considered with respect to the specified nominal values as no manufacturing machine can hold dimensions precisely to the nominal value. In the present description a tolerance of ±0.2 mm for the indicated nominal values is to be considered.

The present description concerns a surgical suction device.

Referring to FIG. 1, the numeral 10 denotes the surgical suction device as a whole.

The surgical suction device 10 comprises:
- a connector 12,
- a surgical cavity insertion tube 14, and
- a suction tip 16.

The surgical cavity insertion tube 14 is connected at a proximal end thereof to the connector 12 and at a distal end thereof to the suction tip 16.

The suction tip 16 comprises an inner hollow shaft 18 and an outer hollow shaft 20 coaxial to each other as shown in FIG. 2. The axial through-cavity of the inner hollow shaft 18 includes a first central opening 22 at a distal end of the inner hollow shaft 18. The outer hollow shaft 20 has an end wall 24 at a distal end thereof, wherein the end wall 24 has a second central opening 26 in axial alignment with the first central opening 22 of the inner hollow shaft 18. The outer hollow shaft 20 has one or more openings 28 on a lateral wall 30 thereof.

The inner hollow shaft 18 and the outer hollow shaft 20 have a cylindrical cross-section.

The inner hollow shaft 18 and the outer hollow shaft 20 can be soldered together or connected by means of a bonding material.

The connector 12 is also axially hollow and comprises a proximal portion 32 and a distal portion 34. The proximal portion 32 of the connector 12 can be smooth or barbed. The proximal portion 32 of the connector 12 is configured for coupling to a tubing, for example a ¼ inch internal diameter tubing (not shown), of a vacuum pump which suctions the fluids from the surgical theatre, or suctions the fluids to a cardiotomy or cell saver reservoir. The distal portion 34 of the connector 12 is instead configured for coupling to the surgical cavity insertion tube 14.

The proximal portion 32 of the connector 12 is substantially frusto-conical, or anyway has a diameter increasing from a first end 36 to a second end 38, wherein the second end 38 is provided with a ridge 40 so that the person connecting the vacuum pump tubing to the surgical cavity insertion tube 14 in theatre is able to see and feel the area which should not be touched, i.e. the surgical cavity insertion tube 14.

The end wall 24 of the outer hollow shaft 20 is shaped to define an apex 42, which is spaced—in an axial direction—from a corresponding end of a cylindrical portion 44 of the inner hollow shaft 18. In a preferred embodiment the end wall 24 of the outer hollow shaft 20 is substantially dome-shaped.

The design of the outer hollow shaft 20 allows the surgical suction device 10 to be more effective than known devices as it ensures that its function is atraumatic and does not suck in tissue.

Figure 3:
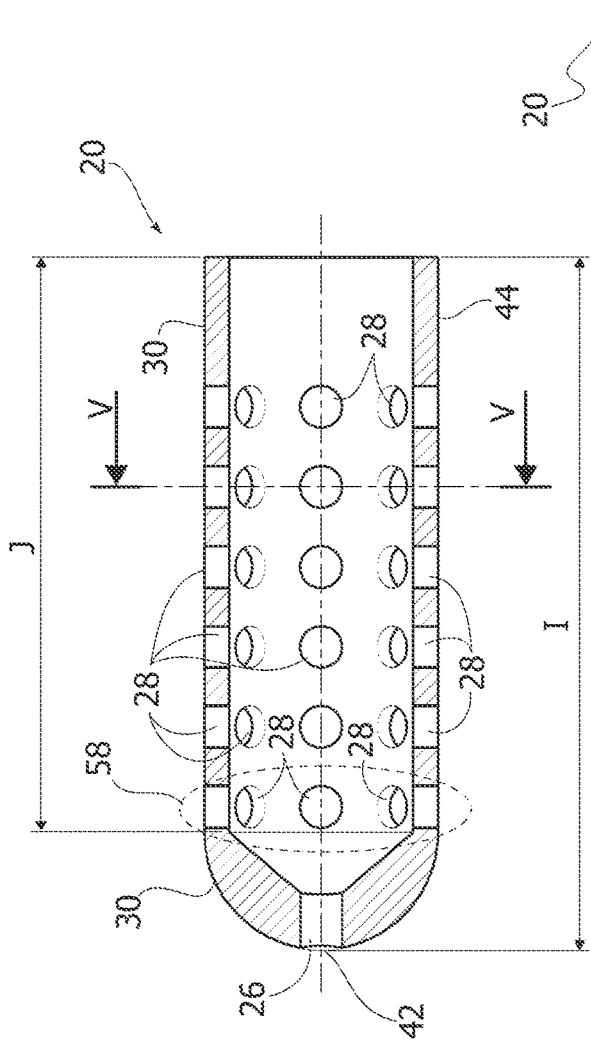
FIG. 3 is a longitudinal section of an outer hollow shaft of a tip of the surgical suction device according to the present invention.
Figure 5:
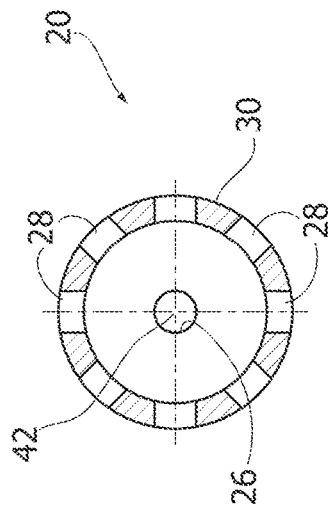
FIG. 5 is a cross-section taken along the line V-V of FIG. 3.
Figure 7:
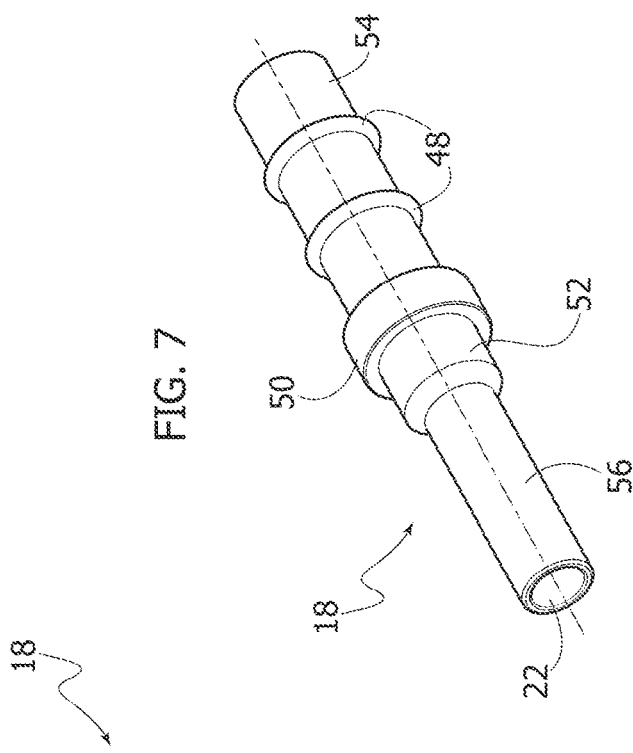
FIG. 7 is a perspective view of the inner hollow shaft of FIG. 6.
Figure 6:
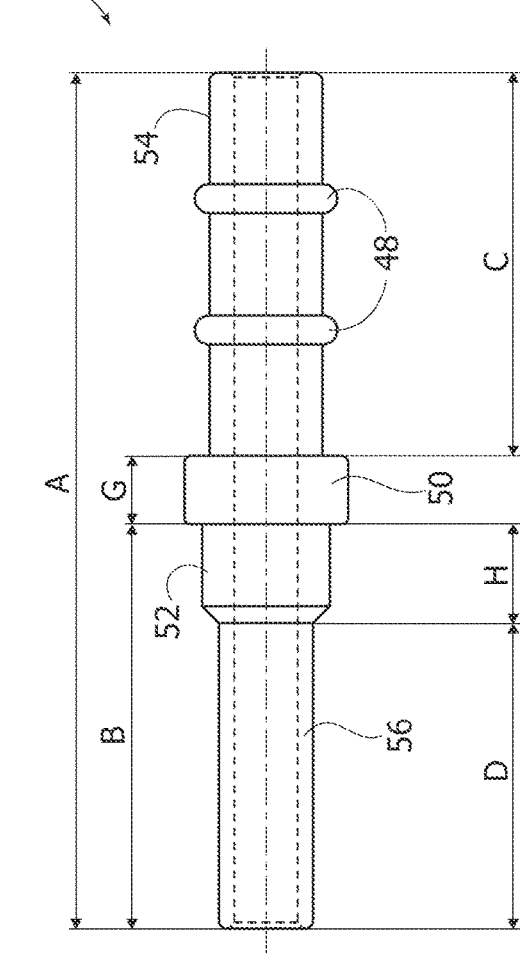
FIG. 6 is a plan view of an inner hollow shaft of a tip of the surgical suction device according to the present invention.
Figure 8:
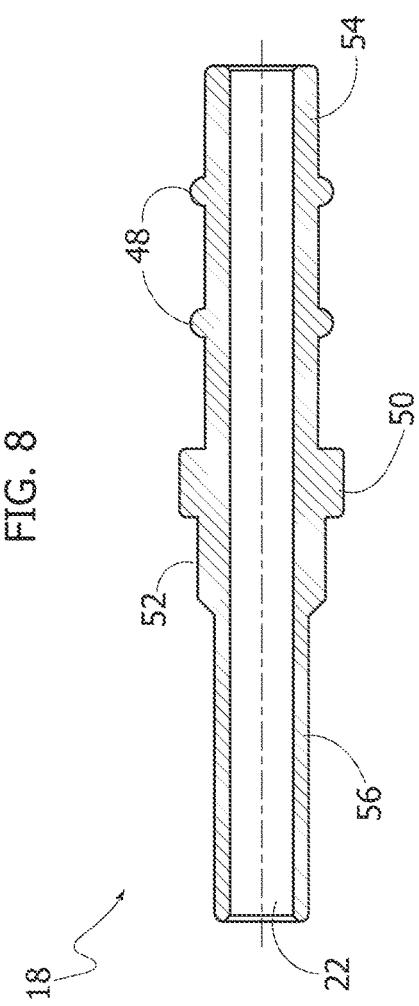
FIG. 8 is a cross-section taken along line VIII-VIII of FIG. 6.

As shown in FIGS. 3 and 4, the one or more openings 28 present on the lateral wall 30 of the outer hollow shaft 20 comprises/comprise at least one series of openings distributed according to a circumference of the outer hollow shaft 20. Preferably, the one or more openings 28 comprises/comprise a plurality of said series of openings, which are spaced from one another in an axial dimension of the outer hollow shaft 20.

The inner hollow shaft 18 is configured, at an end region opposite to the first central opening 22, for coupling with the surgical cavity insertion tube 14.

The inner hollow shaft 18 is configured, at an intermediate region thereof, for coupling with an inner surface 46 of the outer hollow shaft 20.

In one embodiment, the inner hollow shaft 18 has at least one coupling element, such as a ridge 48, located at an end region opposite to the first central opening 22, for coupling within the surgical cavity insertion tube 14. The at least one coupling element or ridge 48 is made of such a size to enable the coupling between the surgical cavity insertion tube 14 and the suction tip 16 to still hold when a 20 N axial force is applied at a rate of 20 mm/min for 15 seconds. The size of the at least one ridge 48 is also determined in function of the Shore hardness and elasticity of the surgical cavity insertion tube 14. The process of ethylene oxide sterilization which the device is subject to before use forms the surgical cavity insertion tube 14 around the at least one ridge 48 creating a strong point of joint.

In one embodiment, the inner hollow shaft 18 has an intermediate flange 50, for abutment, on one side thereof, at the respective end of the outer hollow shaft 20, and for abutment, on the opposite side thereof, at the respective end of the surgical cavity insertion tube 14. The flange has preferably a length G of about 2.0 mm.

In one embodiment, the inner hollow shaft 18 has a tapered portion 52 extending from the flange 50 in the direction of the distal end thereof. The tapered portion 52 has a maximum outer diameter not greater than the inner diameter of the outer hollow shaft 20. Preferably, the tapered section 52 has an outer diameter of about 4.0 mm. The tapered portion has preferably a length H of about 3.5 mm.

In one embodiment, the flange 50 has an outer diameter substantially equal to an outer diameter of the outer hollow shaft 20 at a distal end thereof, and to an outer diameter of the surgical cavity insertion tube 14 at a proximal end thereof, such that—in the assembled condition—the outer surfaces of the elements 50, 20, 14 at issue are substantially flush. In this case there is an atraumatic external transition between the suction tip 16/outer hollow shaft 20 and the surgical cavity insertion tube 14, so that no damages can be determined to the body parts of the patient. In a preferred embodiment, the flange 50 has an outer diameter of about 5.0 mm.

In a preferred embodiment, a proximal portion 54 of the inner hollow shaft 18 (on which the at least one coupling element or ridge 48 is located) has an outer diameter of about 3.6 mm. In a preferred embodiment, a distal portion 56 of the inner hollow shaft 18 (adjacent to the first central opening 22) has an outer diameter of about 3.0 mm. In a preferred embodiment, the inner hollow shaft 18 has an inner diameter of about 2.0 mm.

In a preferred embodiment, the inner hollow shaft 18 has a total length A of about 26.5 mm. In a preferred embodiment, the proximal portion 54 of the inner hollow shaft 18 has a length C of about 12.0 mm. In a preferred embodiment, the distal portion 56 of the inner hollow shaft 18 has a length D of about 9.0 mm.

In a preferred embodiment, the at least one coupling element or ridge 48 is spaced from the proximal end of the inner hollow shaft 18 of about 4.0 mm. In a further preferred embodiment, the inner hollow shaft 18 has at least two ridges 48, spaced from each other of about 4.0 mm.

In one embodiment, the one or more openings 28 comprises/comprise a first series of openings 58 located at a distance of at least 2.0 mm from the apex 42 of the end wall 24.

In one embodiment, the one or more openings 28 have a diameter not greater than 1.5 mm.

In one embodiment, the second central opening 26 is at the apex 42 of the end wall 24.

In one embodiment, the second central opening 26 has a diameter of about 1.0 mm.

In a preferred embodiment, the outer hollow shaft has a total length I of about 15.0 mm. In a preferred embodiment, the cylindrical portion 44 of the outer hollow shaft has a length J of about 13.0 mm.

In one embodiment, a distance K between the distal end 60 of the inner hollow shaft 18 (where the central opening 22 is located) and the apex 42 of the end wall 24 of the outer hollow shaft 20 is not more than 30% of a distance L between the distal end 60 of the inner hollow shaft 18 and a distal edge 62 of the flange 50.

In one embodiment, a distance M between the distal end 60 of the inner hollow shaft 18 and an inner surface 46 of the outer hollow shaft 20 is not more than 0.5 mm. When the distance M is about 1 or 2 mm as the prior art devices then, with the side openings 28 exposed to air, the central opening 26 at the distal end of the outer hollow shaft 20 becomes very inefficient at sucking in blood and other fluids unless the flow of the vacuum pump is very high. Nevertheless, high pump flow rates damage the blood. The preference in theatre is thus to preserve as much of the patient's blood as possible. A sucker with a distance M greater than 0.5 mm draws in more air and this air will cause activation in the blood (haemolysis) and creates the potential for air emboli.

In one embodiment, a distance N between an inner surface of the outer hollow shaft 20 and an outer surface of the inner hollow shaft 18 at the portion 56 thereof is not greater than 1.5 mm.

The dimensions as well as the relative and/or absolute distances between different portions of the inner and outer hollow shafts allow the device object of the present description to not suck air into the suction line and thus not cause blood activation and micro emboli.

In one embodiment, the suction tip 16 has a weight per unit length greater than four times the weight of the same length of the surgical cavity insertion tube 14. The relative weight of the suction tip 16 versus the surgical cavity insertion tube 14 ensures that:

(i) the suction tip 16 sits within the cavity with which it is placed and is not affected by vibration from the roller vacuum pump which is creating the negative pressure to draw the fluid from the patient's surgical cavity;

(ii) the suction tip 16 orientates itself in as near a vertical position as possible. In the vertical position it is most efficient as the central opening 26 is submerged in fluid. A situation where the central opening 26 is exposed to air is not desired as this will draw in air which will mix with the blood and potentially cause activation.

In one embodiment, the outer hollow shaft 20 and the inner hollow shaft 18 are made of a rigid material, preferably surgical steel.

In one embodiment, the surgical cavity insertion tube 14 is flexible and has a Shore hardness lower than or equal to Shore A 75, and greater than or equal to Shore A 40. The Shore hardness of the surgical cavity insertion tube is a critical element to the functionality of the surgical suction device. Having a surgical cavity insertion tube 14 with a Shore hardness lower than Shore A 40 encounters the risk of the surgical cavity insertion tube collapsing (i.e. flattening or kinking) during the suction phase (when a negative pressure is applied) and therefore the device being inoperable. Having surgical cavity insertion tube 14 having a Shore hardness greater than Shore A 75 causes the memory in the surgical cavity insertion tube 14 to potentially lift or flick the surgical sucker out of position when vacuum pump tube to which it is attached is moved, or when the heart lung machine pump is started. A Shore hardness greater than Shore A 75 also causes great difficulty in positioning the suction tip 16 in the surgical theatre.

The invention claimed is:

1. A surgical suction device comprising:
   a connector;
   a surgical cavity insertion tube; and
   a suction tip comprising an inner hollow shaft and an outer hollow shaft coaxial to each other, the inner hollow shaft and the outer hollow shaft being made of a rigid material, the inner hollow shaft having a first central opening at a distal end thereof, the inner hollow shaft comprising an intermediate flange abutting a respective end of the outer hollow shaft on one side thereof and abutting a respective end of the surgical cavity insertion tube at an opposite side thereof, the outer hollow shaft having an end wall at a distal end thereof, the end wall having a second central opening in axial alignment with the first central opening of the inner hollow shaft, the outer hollow shaft having one or more openings on a lateral wall thereof, the suction tip having a weight per unit length greater than four times a weight of a same length of the surgical cavity insertion tube,
   wherein the surgical cavity insertion tube is connected at a proximal end thereof to the connector and at a distal end thereof to the suction tip, and
   wherein a distance between the distal end of the inner hollow shaft and an apex of the end wall of the outer hollow shaft is not more than 30% of a distance between the distal end of the inner hollow shaft and a distal edge of the intermediate flange,
   wherein the distal end of the inner hollow shaft is spaced from an inner surface of the end wall of the outer hollow shaft.

2. The surgical suction device according to claim 1, wherein the end wall of the outer hollow shaft is shaped to define an apex which is spaced from a corresponding end of a cylindrical portion of the inner hollow shaft in an axial direction, preferably the end wall of the outer hollow shaft is substantially dome-shaped.

3. The surgical suction device according to claim 1, wherein the one or more openings comprise at least one series of openings distributed according to a circumference of the outer hollow shaft.

4. The surgical suction device according to claim 3, wherein the one or more openings comprise a plurality of said series of openings spaced from one another in an axial dimension of the outer hollow shaft.

5. The surgical suction device according to claim 1, wherein the inner hollow shaft is configured, at an end region opposite to the first central opening, to couple with the surgical cavity insertion tube.

6. The surgical suction device according to claim 1, wherein the inner hollow shaft is configured, at an intermediate region thereof, to couple with an inner surface of the outer hollow shaft.

7. The surgical suction device according to claim 1, wherein the inner hollow shaft has at least one of the following features:
   at least one coupling element located at an end region opposite to the first central opening, to couple within the surgical cavity insertion tube,
   a flange for abutment, at one side thereof, of the respective end outer hollow shaft, and for abutment, at the opposite side thereof, of the respective end of the surgical cavity insertion tube, and
   a tapered portion extending from a flange in the direction of the distal end and having a maximum outer diameter not greater than an inner diameter of the outer hollow shaft.

8. The surgical suction device according to claim 7, further comprising the flange, the flange having an outer diameter substantially equal to:
   an outer diameter of the outer hollow shaft at a distal end thereof, and
   an outer diameter of the surgical cavity insertion tube at a proximal end thereof.

9. The surgical suction device according to claim 1, wherein the outer hollow shaft has at least one of the following features:
   the one or more openings comprising a first series of openings located at a distance of at least 2.0 mm from an apex of the end wall, the one or more openings having a diameter not greater than 1.5 mm, the second central opening being at an apex of the end wall, and the second central opening having a diameter of about 1.0 mm.

10. The surgical suction device according to claim 1, wherein a distance between the distal end of the inner hollow shaft and an inner surface of the outer hollow shaft is not more than 1.0 mm.

11. The surgical suction device according to claim 1, wherein a distance between an inner surface of the outer hollow shaft and an outer surface of the inner hollow shaft at a portion thereof is not more than 1.5 mm.

12. The surgical suction device according to claim 1, wherein the surgical cavity insertion tube is flexible and has a Shore hardness lower than or equal to Shore A 75 and greater than or equal to Shore A 40.

13. The surgical suction device according to claim 1, wherein the rigid material is surgical steel.

* * * * *